(12) United States Patent
Montoya et al.

(10) Patent No.: US 11,872,126 B2
(45) Date of Patent: *Jan. 16, 2024

(54) IMPLANTABLE VEIN FRAME

(71) Applicant: enVVeno Medical Corporation, Irvine, CA (US)

(72) Inventors: Susan I. Montoya, Irvine, CA (US); Marc Glickman, Irvine, CA (US); Yury Zhivilo, Irvine, CA (US)

(73) Assignee: enVVeno Medical Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,925

(22) Filed: Aug. 12, 2022

(65) Prior Publication Data

US 2022/0378576 A1 Dec. 1, 2022

Related U.S. Application Data

(63) Continuation of application No. 17/183,706, filed on Feb. 24, 2021, now Pat. No. 11,723,766, which is a
(Continued)

(51) Int. Cl.
*A61F 2/82* (2013.01)
*A61F 2/24* (2006.01)
(Continued)

(52) U.S. Cl.
CPC .............. *A61F 2/2418* (2013.01); *A61F 2/06* (2013.01); *A61F 2/2475* (2013.01); *A61F 2/94* (2013.01);
(Continued)

(58) Field of Classification Search
None
See application file for complete search history.

(56) References Cited

U.S. PATENT DOCUMENTS 4,172,295 A  10/1979 Batten
4,922,905 A * 5/1990 Strecker ............... A61F 2/2424
                                                    606/195
(Continued)

FOREIGN PATENT DOCUMENTS

CA    2054728    12/1990
EP    0812580    2/2004
(Continued)

OTHER PUBLICATIONS

European Search Report Application No. 17871027.3, dated Aug. 5, 2020.
(Continued)

*Primary Examiner* — Ann Schillinger
(74) *Attorney, Agent, or Firm* — Kramer Levin Naftalis & Frankel LLP

(57) ABSTRACT

An implantable vein frame is contemplated in which two ring members are rigidly joined in spaced axial alignment via one or more interconnecting members. One of the one or more interconnecting members defines a protruding region that acts upon the implant placed within the frame and/or the vein that the vein frame is placed within to define a sinus region. The implant is placed within and scaffolded by the vein frame, and the vein frame is subsequently inserted within a vein via a venotomy, or interposed between two vein segments via vein interposition graft. The vein frame acts to support the structural integrity of the implant, and to scaffold and anchor the implant in place with the vein.

7 Claims, 4 Drawing Sheets

Related U.S. Application Data continuation of application No. 15/812,070, filed on Nov. 14, 2017, now Pat. No. 10,959,841.

(60) Provisional application No. 62/422,519, filed on Nov. 15, 2016.

(51) Int. Cl.
*A61F 2/06* (2013.01)
*A61F 2/94* (2013.01)
*A61F 2/88* (2006.01)
*A61F 2/915* (2013.01)
*A61L 31/14* (2006.01)
*A61L 31/02* (2006.01)

(52) U.S. Cl.
CPC ....... *A61F 2/2427* (2013.01); *A61F 2002/825* (2013.01); *A61F 2210/00* (2013.01); *A61F 2210/0014* (2013.01); *A61F 2220/0075* (2013.01); *A61F 2230/0006* (2013.01); *A61F 2230/0008* (2013.01); *A61F 2230/0017* (2013.01); *A61F 2230/0021* (2013.01); *A61F 2230/0067* (2013.01); *A61F 2230/0069* (2013.01); *A61F 2230/0086* (2013.01); *A61F 2250/006* (2013.01); *A61F 2250/0026* (2013.01); *A61F 2250/0039* (2013.01)

(56) References Cited

U.S. PATENT DOCUMENTS

| | | | |
|---|---|---|---|
| 5,358,518 A | 10/1994 | Camilli | |
| 7,381,218 B2 | 6/2008 | Schreck | |
| 7,399,315 B2 | 7/2008 | Iobbi | |
| 7,547,322 B2 | 6/2009 | Sarac et al. | |
| 7,563,277 B2 | 7/2009 | Case et al. | |
| 7,637,937 B2 | 12/2009 | Case et al. | |
| 7,947,072 B2 | 5/2011 | Yang et al. | |
| 8,303,649 B2 | 11/2012 | Agnew et al. | |
| 8,372,140 B2 | 2/2013 | Hoffman et al. | |
| 8,403,979 B2 * | 3/2013 | Paul, Jr. | A61F 2/2412 623/1.24 |
| 9,028,542 B2 | 5/2015 | Hill et al. | |
| 9,331,328 B2 | 3/2016 | Eberhardt et al. | |
| 9,308,360 B2 | 4/2016 | Bishop et al. | |
| 10,722,365 B2 | 7/2020 | Chambers et al. | |
| 10,959,841 B2 * | 3/2021 | Montoya | A61F 2/2475 |
| 11,285,243 B2 | 3/2022 | Jaffe | |
| 11,338,064 B2 | 5/2022 | Jaffe | |
| 11,723,766 B2 * | 8/2023 | Montoya | A61F 2/2418 623/1.16 |
| 2004/0034408 A1 | 2/2004 | Majercak et al. | |
| 2005/0154446 A1 | 7/2005 | Phillips et al. | |
| 2006/0111770 A1 | 5/2006 | Pavcnik et al. | |
| 2006/0136042 A1 * | 6/2006 | Holman | A61F 2/07 623/1.42 |
| 2007/0038295 A1 | 2/2007 | Case et al. | |
| 2007/0276467 A1 | 11/2007 | Kalmann | |
| 2008/0183280 A1 * | 7/2008 | Agnew | A61F 2/2475 623/1.24 |
| 2009/0264991 A1 | 10/2009 | Paul, Jr. et al. | |
| 2010/0121423 A1 | 5/2010 | Bernhard et al. | |
| 2011/0118819 A1 | 5/2011 | Contiliano et al. | |
| 2012/0046733 A1 | 2/2012 | von Oepen et al. | |
| 2012/0123529 A1 | 5/2012 | Levi et al. | |
| 2012/0296418 A1 | 11/2012 | Bonynet et al. | |
| 2013/0131793 A1 | 5/2013 | Quadri et al. | |
| 2014/0207229 A1 | 7/2014 | Shoemaker et al. | |
| 2014/0236289 A1 | 8/2014 | Alkhatib | |
| 2016/0250024 A1 | 9/2016 | Hill et al. | |
| 2016/0296331 A1 | 10/2016 | Chung et al. | |
| 2022/0218876 A1 | 7/2022 | Jaffe | |
| 2022/0378576 A1 * | 12/2022 | Montoya | A61F 2/06 |

FOREIGN PATENT DOCUMENTS

| | | |
|---|---|---|
| EP | 1762255 A1 | 3/2007 |
| EP | 2399549 A1 | 12/2011 |
| EP | 2929860 A1 | 10/2015 |
| EP | 2968674 A1 | 1/2016 |
| EP | 2967863 | 9/2016 |
| GB | 2513195 A | 10/2014 |
| JP | 201403835 A | 3/2014 |
| WO | WO2013/176583 A2 | 11/2013 |

OTHER PUBLICATIONS

International Search Report and Written Opinion for PCT Application No. PCT/US2017/061758 dated Jan. 19, 2018, 10 pages.

Extended European Search Report for Application No. 22192496.2 dated Nov. 4, 2022.

* cited by examiner

IMPLANTABLE VEIN FRAME

CROSS-REFERENCE TO RELATED APPLICATIONS

This application is a Continuation of Ser. No. 17/183,706, filed Feb. 24, 2021, which is a Continuation of Ser. No. 15/812,070 filed on Nov. 14, 2017, which issued on Mar. 30, 2021, as U.S. Pat. No. 10,959,841, which relates to and claims the benefit of U.S. Provisional Application No. 62/422,519 filed Nov. 15, 2016, and entitled "IMPLANTABLE VEIN FRAME," the entire disclosure of which is hereby wholly incorporated by reference.

STATEMENT RE: FEDERALLY SPONSORED RESEARCH/DEVELOPMENT

Not Applicable

BACKGROUND

1. Technical Field

The present disclosure relates generally to the field of circulatory system implants. More particularly, the present disclosure relates to support structures for supporting and retaining venous grafts within veins for facilitating vein integrity and venous flow therethrough.

2. Related Art

A number of clinical conditions may necessitate the placement of prosthetic implants for the purpose of improving venous integrity or venous circulation. For example, conditions such as chronic venous insufficient (CVI) or venous reflux may result in significant pain, itching, and swelling, which may consequently give rise to reduced patient mobility and skin ulcerations. Such conditions may result from a number of underlying etiologies, including congenital weakness or absence of valves or vein walls, venous hypertension, and deep vein thrombosis.

Traditionally, these clinical conditions have been treated non-invasively, such as with anti-inflammatory or diuretic medications, with compression garments, or with other noninvasive treatments. Recently, invasive treatments such as the placement of implants such as venous valves are under development as a method of reversing these debilitating conditions. Generally, these invasive treatments are performed via catheterized placement of a non-rigid structure containing an implant, typically a valve, and subsequent anchoring and/or expansion of the non-rigid structure to secure the structure in place within the vein.

These non-rigid structures, however, suffer from a number of deficiencies. For example, there may be a risk of failure of the non-rigid structure supporting the implant to expand and/or anchor properly within the vein, which may lead to unintended migration of the implant. The expansion mechanisms themselves may also represent points of structural weakness that would eventually fail, as those mechanisms may necessarily be less sturdy than the other portions of the implant or support structure for the implant. Further, the expansion mechanisms of such non-rigid support structures may be more susceptible to failure via neointimal proliferation and overgrowth, as they may be required to be formed of more flexible material more prone to applying radial force to the vein, thus increasing the response of neointimal growth Therefore, novel venous implant scaffolding structures that remedy these defects are desirable.

BRIEF SUMMARY

To solve these and other problems, an implantable rigid, non-expandable vein frame is contemplated which is designed to be secured within an elongate section of a vein so as to provide structural support to the vein and for other implants which may be placed within the vein.

According to one embodiment, an implantable rigid, non-expandable vein frame may comprise a first ring member, a second ring member, and at least one interconnecting member disposed between and rigidly interconnecting the first ring member and second ring member in a spaced relation, wherein at least one of the at least one interconnecting members defines a protruding region, at least a portion of the protruding region extending outside of a manifold region defined as a frustoconical volume between and delimited by the first ring member and the second ring member.

According to an exemplary embodiment, at least one interconnecting member may rigidly interconnect the first ring member and second ring member in axial alignment perpendicular to a central axis defined between the respective centers of the first ring member and the second ring member. The first ring member and the second ring member may be substantially circular, have substantially the same internal diameter, and have substantially the same external diameter. The implantable vein frame may also comprise at least three interconnecting members disposed between and rigidly interconnecting the first ring member and second ring member.

In the exemplary embodiment having three interconnecting members, the first interconnecting member may define the protruding region, and the second and third interconnecting members may be substantially linear, disposed in substantially parallel alignment to the central axis, have no portion that protrudes more radially distant from the central axis than the external diameter of the first ring member and the second ring member, and have no portion that intrudes more radially close to the central axis than the internal diameter of the first ring member and the second ring member. The second interconnecting member and the third interconnecting member may be substantially equidistant from the central axis and disposed at a substantially 180° relation about the central axis. The first interconnecting member may be disposed at a substantially 90° relation about the central axis to each of the second interconnecting member and the third interconnecting member.

The exemplary embodiment of an implantable vein frame may also comprise one or more strut members, each of the one or more strut members interconnecting two of the at least three interconnecting members. It may be preferable for the one or more strut members to be arcuately shaped, such that no portion of the one or more strut members protrudes more radially distant from the central axis than the external diameter of the first ring member and the second ring member, and no portion of the one or more struts intrudes more radially close to the central axis than the internal diameter of the first ring member and the second ring member. Each of the one or more strut members may interconnect with one of the at least three interconnecting members at a first interconnection region and interconnect with another of the at least three interconnecting members at a second interconnection region. The first and second interconnection regions may also being disposed non-equidistantly from the first ring member. As may be seen in the exemplary embodiment, the first strut member and the second strut member may both interconnect with the first interconnecting member at a first interconnecting member strut region, the first strut member may interconnects with the second interconnecting member at a second interconnecting member strut region, and the second strut member may interconnect with the third interconnecting member at a third interconnecting member strut region. The second interconnecting member strut region and the third interconnecting member strut region may be substantially equidistant from the first ring member. The first interconnecting member strut region may also be more proximal to the first ring member than the second interconnecting member strut region and the third interconnecting member strut region.

According to other embodiments than the exemplary embodiment, it may be seen variations may exist. For example, it may be seen that at least one of the first ring member and the second ring member may not be substantially circular. It may also be seen that the at least one interconnecting member may rigidly interconnect the first ring member and second ring member in a non-axial alignment. It is further contemplated that other configurations of the vein frame may exist, including for example variations having a third ring member.

The implantable vein frames as presently contemplated may be fabricated from one or more materials chosen from for example: stainless steel, nitinol, a cobalt alloy, titanium, tantalum, plastic. In the exemplary embodiment, the implantable vein frame is fabricated from 316L stainless steel, with the first ring member and the second ring member having an external diameter of from 6 mm to 20 mm.

BRIEF DESCRIPTION OF THE DRAWINGS

These and other features and advantages of the various embodiments disclosed herein are better understood with respect to the following descriptions and drawings, in which.

Common reference numerals are used throughout the drawings and the detailed description to indicate the same elements.

DETAILED DESCRIPTION

According to various aspects of the present disclosure, an improved implantable vein frame is contemplated, the improved implantable vein frame being designed to be secured within or interposed between a section or sections of a vein so as to provide structural support to implants which may be placed within the vein.

Figure 1:
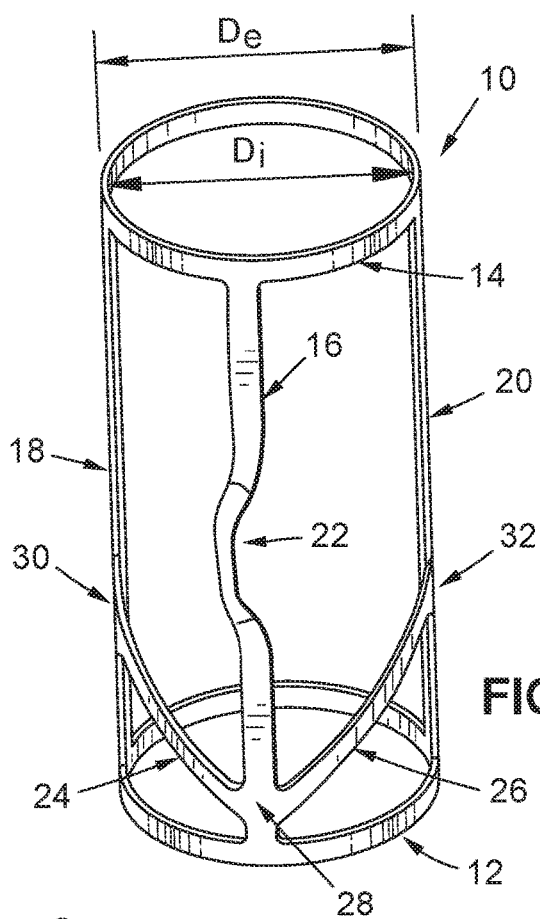
FIG. 1 is a perspective view of an exemplary embodiment of an implantable vein frame.

Turning now to FIG. 1, an exemplary embodiment of a vein frame 10 may be seen. A vein frame 10 of the exemplary embodiment may comprise a first ring member 12 and a second ring member 14, the two ring members being rigidly interconnected by a first interconnecting member 16, a second interconnecting member 18, and a third interconnecting member 20. The first interconnecting member 16 may have a protruding region 22, the first interconnecting member 16 may be interconnected with the second interconnecting member 18 via a first strut member 24, and the first interconnecting member 16 may be interconnected with the third interconnecting member 20 via a second strut member 26. The first strut member 24 and the second strut member 26 may be joined to the first interconnecting member 16 at a first interconnecting member strut region 28, the first strut member 24 may interconnect with the second interconnecting member 18 at a second interconnecting member strut region 30, and the second strut member 24 may interconnect with the third interconnecting member 18 at a third interconnecting member strut region 32.

The first ring member 12 and second ringer member 14 may, in the exemplary embodiment, be circular and fully closed. However, it may be seen that in other embodiments, the configuration of the ring members may vary, without departing from the scope and spirit of the present disclosure. For example, it may be desired to form the ring members in non-circular geometric configurations, such as ovals, ellipses, hexagons, or any other shape suitable for implantation within a vein. It may also be seen that each of the first ring member 12 and second ring member 14 may not necessarily both be configured identically, but may differ. It may further be seen that the ring members may not necessarily be fully enclosed rings, but may be ring-shaped so as to generally conform to and support the vein in which the vein frame 10 may be implanted, while also including gaps or otherwise be being not entirely fully enclosed about their circumferences, and may even comprise, for example but without limitation, spoked or crescent configurations, so long as the function of providing a surface for suturing and support of a valve and for attachment and support of a vein is accomplished. It is generally contemplated in the exemplary embodiment that the ring members are rigid and non-expandable. However, it may be seen that in certain other embodiment, the ring members may be constructed in a manner that is not necessarily rigid and non-expandable. For example, it may be seen that in certain embodiment, it may be a desirable goal to avoiding excess outward pressure on the vein so as to mitigate the likelihood of neointimal growth. While the solution of the exemplary embodiment may be to provide a vein frame 10 with rigid, one-piece ring members having an external diameter De less than or substantially equal to the internal diameter of the vein frame, it may also be seen that in other embodiments, this goal may also be achieved via utilizing modular or configurable ring members that are assembled or otherwise restructured into a final configuration when placed in a vein for which the external diameter De is still less than the internal diameter of the vein, and it may further be seen that such assembling or restructuring may or may not include an expansion.

In the exemplary embodiment, three interconnecting members rigidly interconnect the first ring member 12 and the second ring member 14. The first interconnecting member 16, the second interconnecting member 18, and the third interconnecting member 20 are, in the exemplary embodiment, primarily linear shafts with rectangular cross-sections arranged generally parallel to one another, with the second interconnecting member 18 and the third interconnecting member 20 being in a substantially opposed, 180° relation about the central axis between the midpoints of the circular ring members to one another, with the first interconnecting member 16 being disposed at a substantially 90° relation about the ring members to both the second interconnecting member 18 and the third interconnecting member 20. However, it may be seen that in other embodiments, the number and configurations of the one or more interconnecting member(s) may vary, without departing from the scope and spirit of the present disclosure. For example, it may be seen that variations may exist in which only one interconnecting member is utilized, or only two, or more than three interconnecting members, or that the interconnecting members are not necessarily linear or parallel shafts, or do not necessarily have rectangular cross-sections. In certain variations, it may even be seen that the interconnecting member(s) may comprise a mesh, lattice or even a solid annular or semi-annular wall. It may thus be seen that the exact configuration of the interconnecting member(s) may be substantially variable, so long as the function of serving as a scaffold for the vein, implant, and for rigidly interconnecting the first ring member 12 and the second ring member 14 in a spaced relation is accomplished.

In the exemplary embodiment, the first interconnecting member 16 has a protruding region 22 that protrudes outward from the vein frame 10 at about a midpoint between the two ring members. The protruding region 22 is, in the exemplary embodiment, defined by a outward curve of the first interconnecting member 16, and is sized and configured to accommodate a leaflet of a monocuspid valve. In other embodiments, however, variations of the protruding region 22 may exist. For example, the protruding region 22 may be located at a different location, or there may be more than one protruding region 22 on one or more interconnecting member, or the protruding region 22 may have a different configuration, such as being locating more proximal to one ring member than the other, or the protruding region may be differently sized or configured. What is important for the protruding region 22 is that at least a portion of the protruding region 22 extends outward from the vein frame 10. As may be seen, depending on the configurations of the ring members and the protruding region 22 extends outside of a manifold region defined as a frustoconical volume between and delimited by the first ring member 12 and the second ring member 14, so that when the vein frame 10 is implanted within a vein or has an implant placed within it, the protruding region 22 acts to sculpt either the vein and/or the implant outwardly so as to define a sinus region spacing between them defined by the configuration of the interconnecting member(s), the manifold region will correspondingly differ in shape as well, though the shape will remain a frustoconical volume, i.e., the shape that the vein will take when stretched over the ring members.

In the exemplary embodiment, the second interconnecting member 18 and third interconnecting member 20 are disposed in a substantially 180° relation about the central axis to each other, and in 90° relation to the first interconnecting member 16. However, it may be seen that in other embodiments, the positioning of various of the interconnecting members, if more than one, may vary.

In the exemplary embodiment, the interconnecting members are further rigidly interconnected with one another by a first strut member 24 and a second strut member 26. The first strut member 24 and the second strut member 26, in the exemplary embodiment, are both joined to the first interconnecting member 16 at a first interconnecting member strut region 28. The first strut member 24 is joined at its other end to the second interconnecting member 18 at a second interconnecting member strut region 30. The second strut member 26 is joined at its other end to the third interconnecting member 20 at a third interconnecting member strut region 32. The second interconnecting member strut region 30 and the third interconnecting member strut region 32 are disposed at substantially similar distances from the first ring member 12, while the first interconnecting member strut region 28 is disposed more near to the first ring member 12 than both of the second interconnecting member strut region 30 and the third interconnecting member strut region 32. In the exemplary embodiment wherein both ring members are circular, the same size, and in axial alignment perpendicular to a central axis defined between their respective centers, the first strut member 24 and the second strut member 26 are both acutely shaped in a curved configuration so that no portion of the one or more strut members protrudes more radially distant from the central axis than the external diameters De of the first ring member 12 and the second ring member 14, and so that no portion of the one or more strut members intrudes more radially close to the central axis than the internal diameters Di of the first ring member 12 and the second ring member 14. However, it may be seen that in other embodiments than the exemplary embodiment shown, the interconnecting members may be interconnected in other ways to one another, or not interconnected, depending on the nature and purpose of that specific embodiment. For example, it is to be understood that strut members may, for example, protrude more radially inward than the internal diameters Di of various ring members, up to and including cross-linking various interconnecting members even through the central axis, if the embodiment has one. Such internal cross-linking may, for example, serve to provide further internal anchoring points for a material to be supported by the vein frame 10.

In the exemplary embodiment, the vein frame 10 and its components are cut from a single piece of 316L stainless steel. However, it may be seen that in other embodiments, the vein frame 10 and/or it components may be fabricated of other or multiple materials using a variety of fabrication methods generally known in the industry, and such components may be joined together after fabrication. For example, according to certain embodiments, the vein frame 10 may be formed from stainless steel, nitinol, a cobalt alloy, titanium, tantalum, plastic, or combinations thereof.

Furthermore, in the exemplary embodiment, the first ring member 12 and second ring member 14 are formed to have an external diameter De of between 6 mm to 20 mm. However, it may be seen that in other embodiments, the ring members may be formed to be of other dimensions, including non-circular dimensions.

It may also be seen that in other embodiments than the exemplary one, other configurations of a vein frame 10 and the components thereof are possible. For example, but without limitation, a vein frame 10 may have three or more ring members, with such three or more ring members being arranged in multiple configurations. One such possible configuration may include a branching configuration whereby the vein frame 10 is configured to receive an implant meant for placement at a region of venous flow where two or more channels of venous flow converge, or where one or more channels of venous flow diverge. It may thus be seen that the inclusion of three or more ring members may facilitate placement of such an implant configured for such branching regions.

Figure 2:
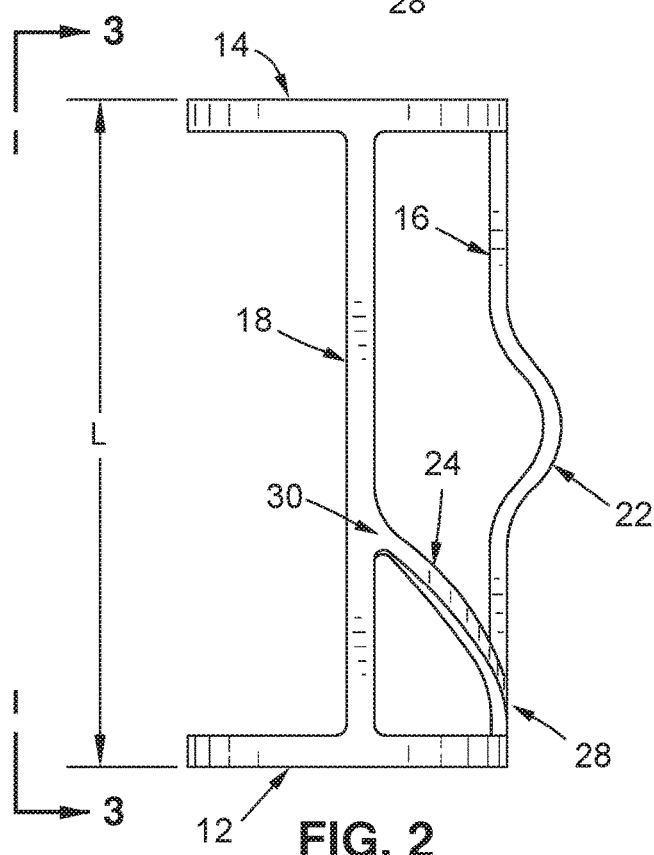
FIG. 2 is a side view of an exemplary embodiment of an implantable vein frame.

Turning now to FIG. 2, in the exemplary embodiment, the ring members are aligned and kept apart by their rigid interconnection with the interconnecting members in a spaced relation from one another, which is understood to mean that there is some distance L between the two rings—i.e., one ring is not enclosed within the other.

It may also be seen in the view of FIG. 2 how the protruding region 22 extends further outside the manifold region defined as the frustoconical volume between and delimited by the first ring member 12 and the second ring member 14.

Figure 3:
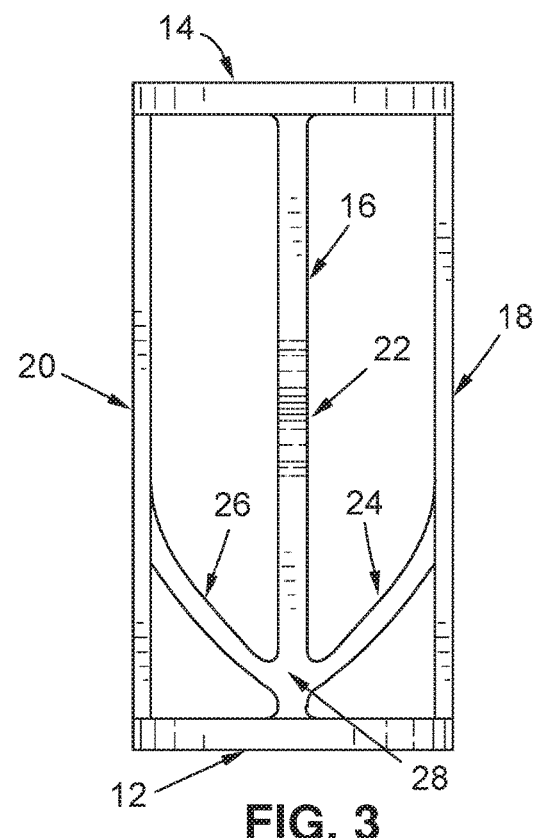
FIG. 3 is a top view of an exemplary embodiment of an implantable vein frame.

Turning now to FIG. 3, it may further be seen how, in the exemplary embodiment, the first strut member 24 and the second strut member 26 (positioned behind and in alignment with the first strut member 24) are arcuately curved such that no portion of either strut member protrudes more outwardly distant from the central axis than any portion of either ring member, and such that no portion of either strut member intrudes more near to the central axis than any portion of either ring member.

Figure 4:
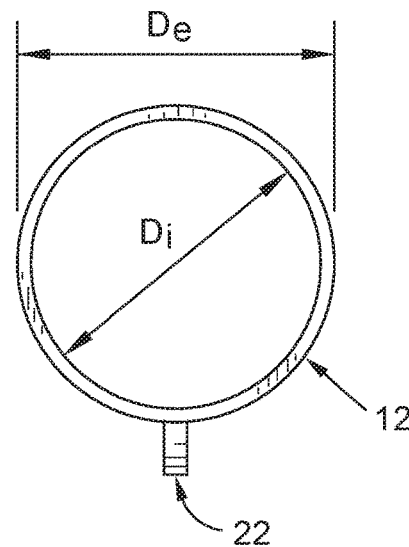
FIG. 4 is a front view of an exemplary embodiment of an implantable vein frame.

Turning now to FIG. 4, it may be seen in more detail how in the exemplary embodiments, the first ring member 12 and the second ring member 14 are both circular and have substantially the same dimensions. Further, it may be seen how the two ring members are disposed in axial alignment perpendicular to a central axis defined between respective centers of the first ring member and the second ring member, as the front view of FIG. 4 shows that the first ring member 12 superposed over the second ring member 14. The internal diameter Di and external diameter De of the ring members of the exemplary embodiment is also better visualized. It may also be seen, however, that in embodiment other than the exemplary embodiments, including embodiments in which the ring members are circular, non-circular, or partially circular, the two ring members may not be disposed in axial alignment, but may instead be disposed in other alignments, such as an offset non-axial parallel alignment, a mirrored, non-axial alignment, non-parallel alignment, a non-mirrored, non-axial, non-parallel alignment. Further, the ring members in these other embodiments may have similar shapes but dissimilar sizes, such as circles with dissimilar internal and external diameters.

Likewise, it may also be more easily seen by the illustration of FIG. 4 how the protruding region 22 extends outside of the manifold region defined as the frustoconical volume between and delimited by the first ring member 12 and the second ring member 14. In the case of the exemplary embodiment, this frustoconical volume is the cylinder having a length L and a diameter De. However, it may be seen in other embodiments that the frustoconical volume may be shapes other than a cylinder, and may not necessarily even be a circular or other conic segment, but may also be, for example, a pyramid segment, square pyramid segment, or other geometric volume. Likewise, it may be seen how even in embodiments with ring members that are not fully enclosed, a frustoconical volume may still be defined.

Figure 5:
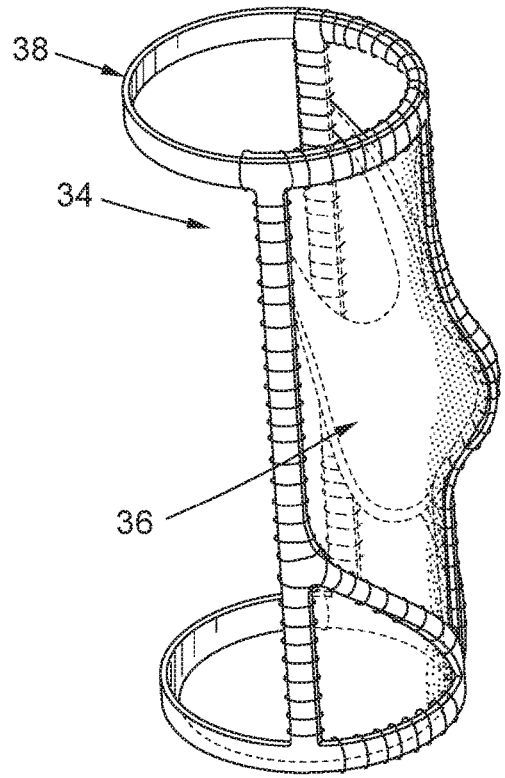
FIG. 5 is a perspective view of an exemplary embodiment of an implantable vein frame having a monocupsid valve contained within.

Turning now to FIG. 5, it may be seen how an implant 34 may be contained by and within the vein frame 10 of the exemplary embodiment. According to one embodiment, the implant 34 is a monocuspid valve which contains a single leaflet 36, the implant 34 being sized to be of similar length as the vein frame 10 of the exemplary embodiment. The implant 34 may be scaffolded by the vein frame 10 by the placement of sutures 38 through the implant 34 and around the material of the vein frame 10. However, it may be seen that in other embodiments, the implant may be other than a monocuspid valve that contains a single leaflet 34. Indeed, it may be seen that the vein frame 10 as presently disclosed and contemplated, including embodiments in addition to the exemplary embodiment, may be suitable for scaffolding any sort of implant 34 which may be desired to be placed within a vein, not just valve implants, and further the implant 34 may be suitable for placement anywhere that the vein frame 10 may be placed. The implant 34 is, in the exemplary embodiment, a porcine derived xenograph. However, may also be seen that the implant 34 may be, for example but without limitation, an autograph, allograph, other xenograph, an entirely artificial implant, or combinations thereof.

Figure 6:
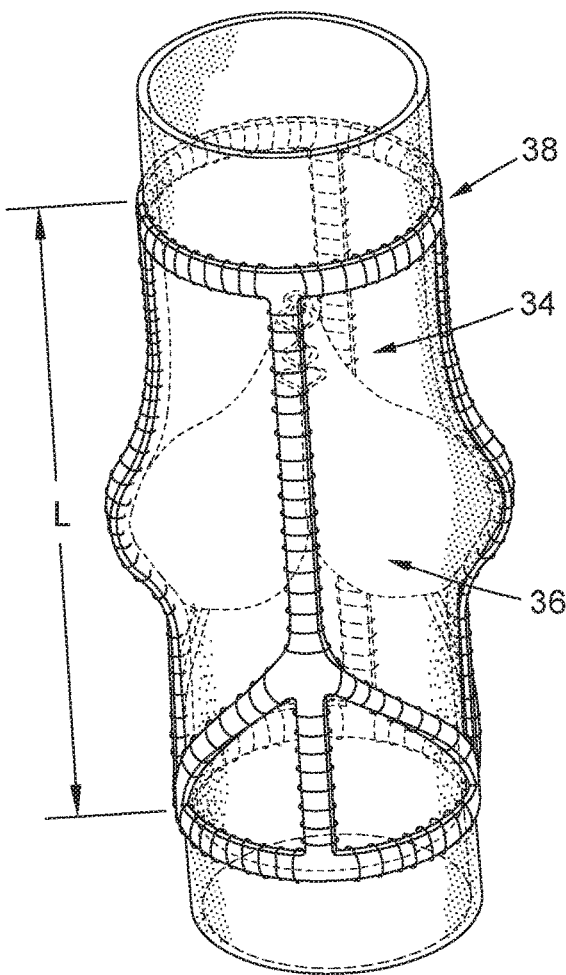
FIG. 6 is a perspective view of another embodiment of an implantable vein frame having a bicuspid valve contained within.

Turning now to FIG. 6, an alternative embodiment of a vein frame 10 is illustrated, with this alternative embodiment having four interconnecting members at substantially 90° relation relative to one another, with two protruding regions 22 at two of the opposed interconnecting members, as well as four strut members. It thus may be seen that this alternative embodiment may be preferable where it may be desirable, for example, for the implant 34 to have or comprise a bicuspid valve, as a vein frame 10 with two protruding regions 22 may be more suitable for accommodating the two leaflets 34 of the bicuspid valve. It may also by the illustrated alternative embodiment that that it may be preferable for the length of the implant 34 to not be contained within the length L of the vein frame 10, but rather may extend beyond the vein frame 10. Such an embodiment may be useful when, for instance, the vein frame is configured for placement not within a vein via a venotomy, as in the implant of the embodiment shown in FIG. 5, but rather for placement between two portions of a vein via a vein interposition graft.

Figure 7:
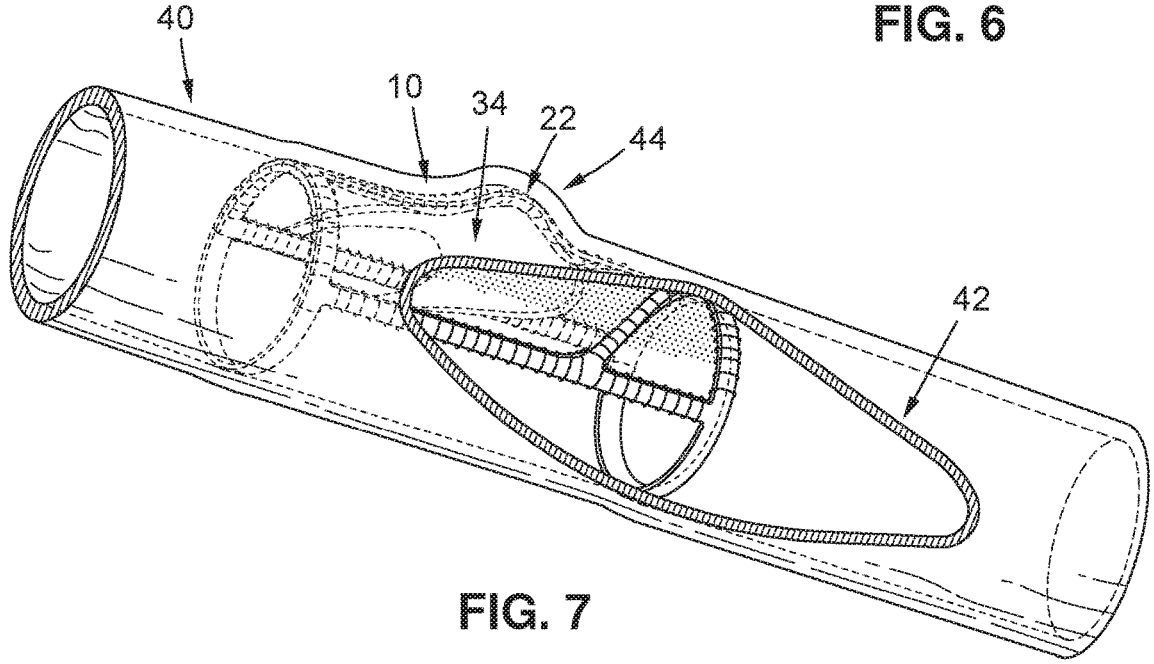
FIG. 7 is a perspective view of an exemplary embodiment of an implantable vein frame having a valve contained within being implanted in a vein via a venotomy.

Turning now to FIG. 7, an illustration of placement of a vein frame 10 of the exemplary embodiment having an implant 34 sutured within inside of a vein 40 via a venotomy is shown. It may be seen how an incision 42 may be made in the vein 40, and the vein frame 10 may be placed within. It may further be seen how the protruding region 22 may act to support the sinus of the valve component. The vein frame 10 may be configured to have a greater external diameter De than the general diameter of the vein 40, or a reduced external diameter De relative to the general diameter of the vein 40. For example, it may be seen that the when the size of the external diameter De is relatively similar to or less than the vein 40, the pressure exerted by the vein frame 10 on the vein 40 may be reduced relative to conventional expandable vein frames, which may mitigate the likelihood of neointimal growth. For such embodiments, prevention of lateral travel within the vein may be achieved by, for example, suturing of the vein frame 10 within the vein, or other methods known in the art. Likewise, it may be seen that in embodiments where the external diameter De is greater than the diameter of the vein 40, the size of the vein frame alone may reduce the susceptibility of the vein frame 10 to travel laterally within the vein 40 following closure of the incision 42, and suturing within the vein may not be necessary. It may be seen that the vein frame 10 may be secured within the vein 40 following closure of the incision 42 by any known methods, not just via snugness of fit or suturing.

Figure 8:
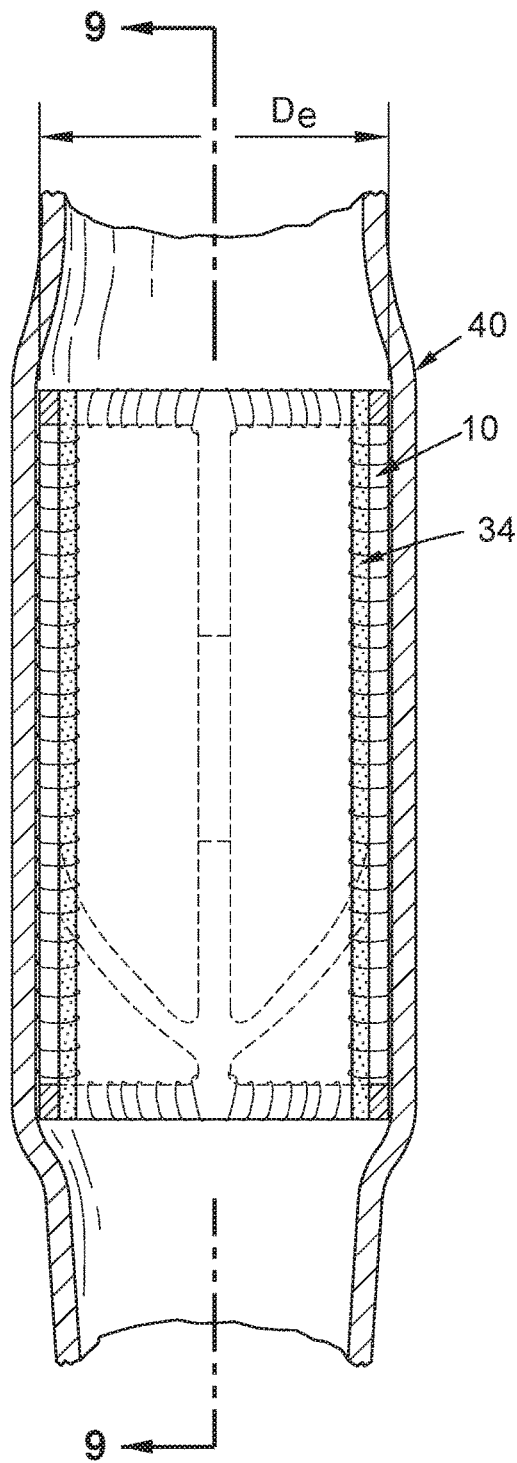
FIG. 8 is a top view of an exemplary embodiment of an implantable vein frame having a valve contained within following implantation within a vein.

Turning now to FIG. 8, a top view of an exemplary embodiment of a vein frame 10 placed within a vein 40 via a venotomy is shown. As may be seen, the vein frame 10 may be sized to have an external diameter De that is less than, equal to, or greater than the general internal diameter of the vein 40 in which it is placed, and as such may or may not elastically deform the vein 40 via its placement.

Figure 9:
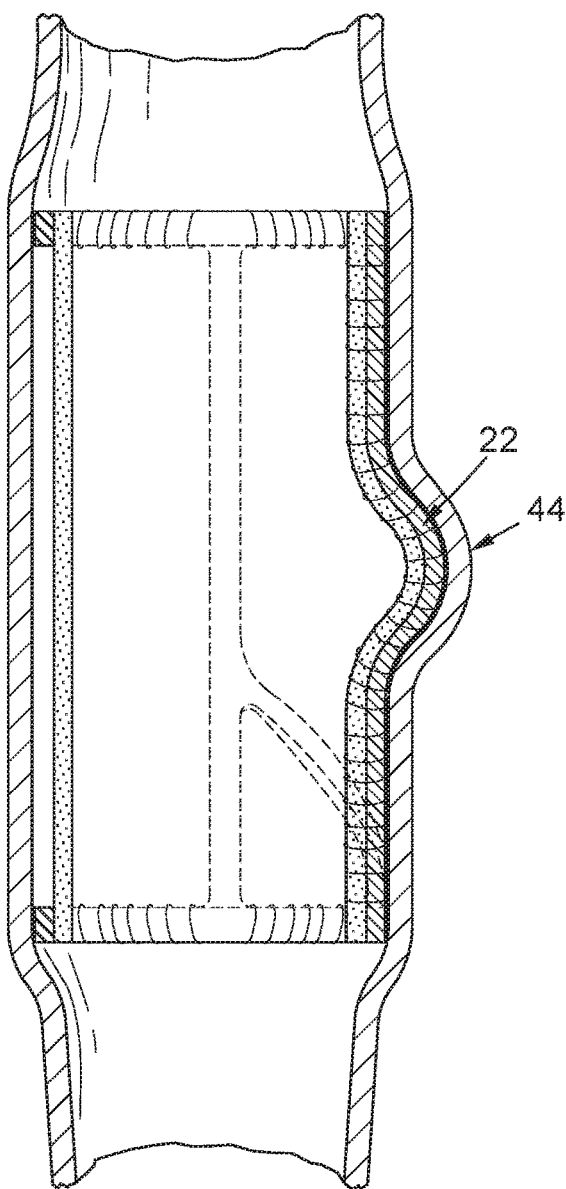
FIG. 9 is a side view of an exemplary embodiment of an implantable vein frame having a valve contained within following implantation within a vein.

Turning now to FIG. 9, a side view of the vein frame 10 of the exemplary embodiment placed within a vein 40 via a venotomy is shown. As may be seen, the protruding region 22 acts to support a sinus 44 via its interaction with the corresponding valve structure.

Figure 10:
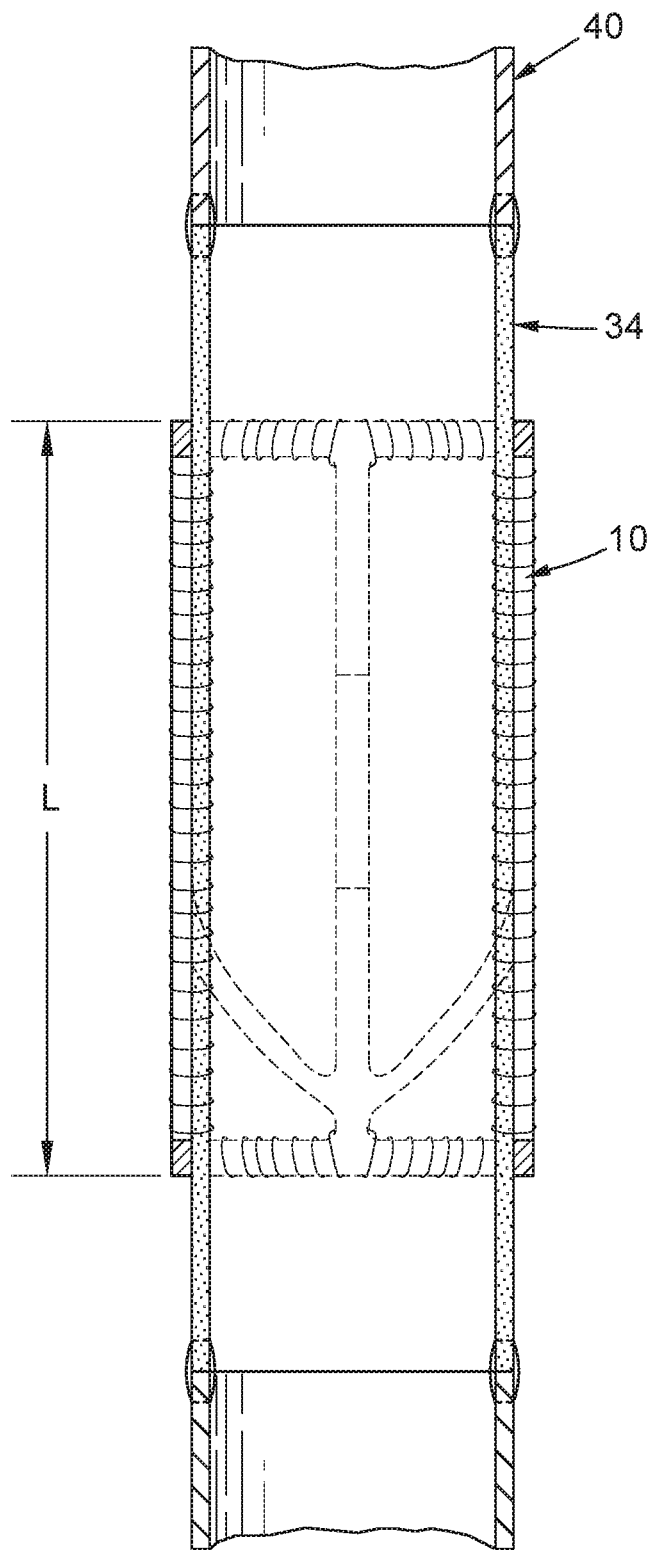
FIG. 10 is a top view of an exemplary embodiment of an implantable vein frame having another valve contained within following implantation via a vein interposition graft.

Turning now to FIG. 10, a top view of the alternate embodiment of an implant 34 within a vein frame 10 is shown, wherein the implant 34 is sized to be longer than the length L of the vein frame 10 in order to leave an extended region of the material of the implant beyond the ring members of the vein frame 10. As may be seen, such an alternate embodiment may be useful for positioning the vein frame 10 and implant 34 within the path of venous flow via a vein interposition graft, whereby the implant 34 scaffolded by the vein frame 10 is placed between two segments of a vein 40, and secured to those two segments so that venous flow is permitted to pass therethrough. The method of securing the implant to the vein may be any method known in the art, such as for example, suturing.

The above description is given by way of example, and not limitation. Given the above disclosure, one skilled in the art could devise variations that are within the scope and spirit of the invention disclosed herein. Further, the various features of the embodiments disclosed herein can be used alone, or in varying combinations with each other and are not intended to be limited to the specific combination described herein. Thus, the scope of the claims is not to be limited by the exemplary embodiments.

What is claimed is:

1. A vein frame and valve assembly, comprising:
   a distal inlet member;
   a proximal outlet member;
   at least one rigid and non-expandable axial support member interconnecting said inlet member and said outlet member, wherein said at least one axial member includes at least one region along its length that protrudes beyond the region defined by a frustoconical volume between and delimited by said inlet member and outlet member; and
   a valve attached to said at least one axial support member, wherein said valve is positioned between said inlet member and outlet member; and
   at least one of the inlet or outlet members are rigid and non-expandable.

2. The vein frame and valve assembly of claim 1, further comprising a valve selected from the group consisting of a monocuspid valve, a bicuspid valve, a leaflet of a mono cuspid valve, and a leaflet of a bicuspid valve.

3. The vein frame and valve assembly of claim 1, further comprising at least one strut member that is connected to said at least one axial support member and to said inlet member or outlet member.

4. The vein frame and valve assembly of claim 3, wherein said sinus of said valve is protected from deformation by the protruding region of said axial support member, wherein said axial support member is rigid and non-expandable.

5. The vein frame and valve assembly of claim 1, wherein said inlet member and said outlet member are substantially circular, have substantially the same internal diameter, and have substantially the same external diameter.

6. The vein frame and valve assembly of claim 1, further comprising at least three axial support members and said valve is positioned in said protruding region to support a sinus of said valve.

7. The vein frame and valve assembly of claim 1, wherein said valve is larger than the diameter of said inlet and outlet members.

\* \* \* \* \*